US008987399B2

(12) United States Patent
Thomas et al.

(10) Patent No.: US 8,987,399 B2
(45) Date of Patent: *Mar. 24, 2015

(54) AZEOTROPES OF ISOBUTYLENE WITH FLUORO-OLEFINS

(71) Applicant: Honeywell International, Inc., Morristown, NJ (US)

(72) Inventors: Raymond H. Thomas, Pendleton, NY (US); Hang T. Pham, Amherst, NY (US); Rajiv R. Singh, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/801,177

(22) Filed: Mar. 13, 2013

(65) Prior Publication Data

US 2014/0128559 A1  May 8, 2014

Related U.S. Application Data

(60) Provisional application No. 61/724,291, filed on Nov. 8, 2012.

(51) Int. Cl.
C08F 10/10 (2006.01)
C08F 110/10 (2006.01)
C08F 2/06 (2006.01)
C07C 21/18 (2006.01)
C09K 3/00 (2006.01)
C08F 110/06 (2006.01)

(52) U.S. Cl.
CPC . C08F 2/06 (2013.01); C07C 21/18 (2013.01); C09K 3/00 (2013.01); C08F 110/06 (2013.01)
USPC .......................... 526/348.7; 526/206; 252/364

(58) Field of Classification Search
CPC .................................. C07C 21/18; C08F 2/06
USPC ....................... 510/412, 408; 252/69, 67, 364; 526/348.7, 206
See application file for complete search history.

(56) References Cited

U.S. PATENT DOCUMENTS

| 5,182,040 | A | 1/1993 | Bartlett et al. | |
| 5,648,017 | A | 7/1997 | Bartlett et al. | |
| 7,402,636 | B1 | 7/2008 | Shaffer et al. | |
| 7,423,100 | B2 * | 9/2008 | McDonald et al. | 526/89 |
| 7,423,188 | B2 * | 9/2008 | Miller et al. | 570/155 |
| 7,700,004 | B2 | 4/2010 | Nappa et al. | |
| 7,781,547 | B2 * | 8/2010 | Chen et al. | 526/88 |
| 8,008,244 | B2 * | 8/2011 | Knopeck et al. | 510/408 |
| 8,273,928 | B2 * | 9/2012 | Knapp et al. | 570/136 |
| 2005/0101751 | A1 | 5/2005 | Shaffer et al. | |
| 2008/0103272 | A1 | 5/2008 | Chen et al. | |
| 2009/0305876 | A1 | 12/2009 | Singh et al. | |
| 2010/0081836 | A1 | 4/2010 | Parslow et al. | |
| 2010/0181524 | A1 | 7/2010 | Elsheikh et al. | |
| 2013/0158218 | A1 | 6/2013 | Thomas et al. | |
| 2014/0128559 | A1 * | 5/2014 | Thomas et al. | 526/206 |
| 2014/0128561 | A1 * | 5/2014 | Thomas et al. | 526/255 |

FOREIGN PATENT DOCUMENTS

WO  WO 2012/106565  8/2012

OTHER PUBLICATIONS

Dong, X.; Gong, M.; Shen, J.; Wu, J. J. Chem. Eng. Data, 2012, 57, 541-544.*
Akasaka, R. Int. J. Air-Cond. Ref., 2011, 19, 93-97.*
Ryo Akasaka, "Vapor-Liquid Equilibrium Modeling for Mixtures of HFC-32 + Isobutane and HFC-32 + HFO-1234ze (E)", International Journal of Air-Conditioning and Refridgeration (2011), vol. 19, No. 2, pp. 93-97.
Dong, Xueqiang, et al., "Vapor-Liquid Equilibria of the trans-1,3,3-Tetrafluoropropene (R1234ze(E) + Isobutane (R600a) System of Various Temperatures from (258.150 to 288.150) K", Journal of Chemical and Engineering Data, 2012, vol. 57, No. 2, pp. 541-544 (Published online Dec. 8, 2011).
Bahadur, Maneesh, et al., "Dimethylaluminum chloride catalyzed living isobutylene polymerization", Macromolecules 2000, vol. 33, No. 26 pp. 9548-9552.
Chung, T.C., et al., "Carbocationic polumerization of isobutylene by using supported Lewis acid catalyst on polypropylene", Polymer Bulletin 1992, vol. 28, No. 2 pp. 123-128.
Storey, Robson F., et al., "Kinetic study of the living cationic polymerization of isobutylene using a dicumyl chloride/TiC14/pyridine initiating system", Macromolecules 1995, vol. 28, No. 12, pp. 4055-4061.

* cited by examiner

Primary Examiner — Rip A. Lee
(74) Attorney, Agent, or Firm — Erika Wilson

(57) ABSTRACT

Azeotropic or azeotrope-like compositions of the present invention include trans-1,3,3,3-tetrafluoroprop-1-ene and isobutylene. The azeotropic or azeotrope-like compositions can be used in polymerization processes, including slurry polymerization processes.

17 Claims, No Drawings

AZEOTROPES OF ISOBUTYLENE WITH FLUORO-OLEFINS

CROSS REFERENCE TO RELATED APPLICATION

The present application claims priority under 35 U.S.C. §119(e) to U.S. Provisional Patent Application No. 61/724,291, filed on Nov. 8, 2012, the disclosure of which is incorporated herein by reference in its entirety.

FIELD OF THE INVENTION

The present invention relates to the production of polyalpha-olefins (PAOs), polyisobutylenes (PIBs), and copolymers thereof. More particularly, the present invention relates to the use of an azeotropic or azeotrope-like composition, which includes trans-1,3,3,3-tetrafluoroprop-1-ene (otherwise referred to as "trans-HFO-1234ze") as a solvent or diluent in the process of producing polyisobutylene and its copolymers.

DESCRIPTION OF RELATED ART

Methyl chloride is commonly used as a solvent or diluent in the process of producing polyisobutylene and its copolymers. For example, slurry polymerization processes in methyl chloride are used in the production of high molecular weight polyisobutylene and isobutylene-isoprene butyl rubber polymers. Likewise, polymerizations of isobutylene and para-methylstyrene are also conducted using methyl chloride. Similarly, star-branched butyl rubber is also produced using methyl chloride.

Typically, such polymerization processes use methyl chloride at low temperatures, generally at about −90° C., as the diluent for the reaction mixture. Methyl chloride is employed for a variety of reasons, including that it dissolves the monomers and the catalyst, e.g., aluminum chloride, but not the polymer product.

However, there are a number of problems associated with the polymerization in methyl chloride, for example, the tendency of the polymer particles in the reactor to agglomerate with each other and to collect on the reactor wall, heat transfer surfaces, impeller(s), and the agitator(s)/pump(s). The rate of agglomeration increases rapidly as reaction temperature rises. Agglomerated particles tend to adhere to and grow and plate-out on all surfaces they contact, such as reactor discharge lines, as well as any heat transfer equipment being used to remove the exothermic heat of polymerization, which is critical since low temperature reaction conditions must be maintained.

SUMMARY OF THE INVENTION

The present invention relates to azeotropic or azeotrope-like compositions that include trans-HFO-1234ze and isobutylene. The azeotropic or azeotrope-like compositions can be used as solvents or diluents in polymerization processes, including slurry polymerization processes.

In one aspect, an azeotropic or azeotrope-like composition is provided that includes, consists essentially of, or consists of, trans-HFO-1234ze and isobutylene.

In another aspect, a polymerization medium suitable to polymerize one or more monomers to form a polymer is provided that includes at least one Lewis acid, isobutylene, and trans-HFO-1234ze.

DETAILED DESCRIPTION

Azeotropic or azeotrope-like compositions of the present invention include, consist essentially of, or consist of, isobutylene and trans-HFO-1234ze. Trans-HFO-1234ze is also known as R-1234ze. The azeotropic or azeotrope-like compositions can be used as solvents or diluents in polymerization processes, including slurry polymerization processes. In at least some examples, the azeotropic or azeotrope-like compositions can be used as a solvent or diluent in the production of polymers that can include, for example, polyalpha-olefins (PAOs), polyisobutylenes (PIBs), and copolymers thereof. Nonlimiting examples of such polymers include (poly)isobutylene homopolymers, isobutylene-isoprene (butyl rubber) copolymers, isobutylene and alkylstyrene copolymers, and star-branched butyl rubber terpolymers.

There is concern for the environment in terms of global warming and ozone depletion. Trans-HFO-1234ze has zero ozone depletion potential (ODP). Furthermore, HFO-1234ze has a global warming potential (GWP) of 6, which is quite low.

The toxicity and flammability of hydrofluorocarbons and hydrofluoro-olefins is also of potential concern. Hydrofluoro-olefins, in particular, are often toxic and flammable; however, trans-HFO-1234ze is both non-toxic and is not highly flammable. Additionally, trans-HFO-1234ze, can reduce the flammability of isobutylene when in an azeotropic or azeotrope-like composition of the present invention.

As used herein, the term "azeotropic or azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant-boiling and cannot be separated during a phase change.

Azeotropic compositions are constant boiling compositions, and azeotrope-like compositions are constant boiling or essentially constant boiling. In other words, for azeotropic and azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotropic or azeotrope-like compositions of the present invention within the indicated ranges, as well as, certain compositions outside these ranges, are azeotrope-like.

The azeotropic or azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotropic or azeotrope-life compositions is that there is a range of compositions containing the same components in varying proportions that are azeotrope-like or constant boiling. All such compositions are intended to be covered by the terms "azeotropic or azeotrope-like" and "constant boiling." As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

It is well-recognized in the art that it is not possible to predict the formation of azeotropes, as indicated, for example, in U.S. Pat. No. 5,648,017 (column 3, lines 64-65) and U.S. Pat. No. 5,182,040 (column 3, lines 62-63), both of which are incorporated herein by reference. Applicants have discovered unexpectedly that trans-HFO-1234ze and isobutylene form azeotropic and azeotrope-like compositions.

According to certain preferred embodiments, the azeotropic or azeotrope-like compositions of the present invention comprise, and consist essentially of, or consist of, effective amounts of trans-HFO-1234ze and isobutylene. The term "effective amounts" as used herein refers to the amount of each component which, upon combination with the other component, results in the formation of an azeotropic or azeotrope-like composition. Any of a wide variety of methods known in the art for combining the components to form a composition can be adapted for use in the present methods to produce an azeotropic or azeotrope-like composition. For example, HFO-1234ze and isobutylene can be mixed, blended, or otherwise contacted by hand and/or by machine, as part of a batch or continuous reaction and/or process, or via combinations of two or more such steps. In light of the disclosure herein, those of skill in the art will be readily able to prepare azeotropic or azeotrope-like compositions according to the present invention without undue experimentation.

In examples where azeotropic or azeotrope-like compositions of the present invention comprise, consist essentially of, or consist of, isobutylene and HFO-1234ze, the HFO-1234ze can be present in an amount from about 82% by weight of the composition to about 96% by weight of the composition, and more preferably, between about 85% by weight of the composition to about 91% by weight of the composition. As illustrated more fully in Example 1 below, the azeotrope has been found to occur when the HFO-1234ze is present in an amount between about 85% by weight of the composition to about 91% by weight of the composition, i.e., at about a concentration of 88% by weight. The boiling point of the azeotrope was experimentally measured to be at about −20.23° C. at a pressure of about 1 atmosphere.

As used herein, the term "about" refers to an approximate amount that falls within an acceptable range of experimental error. For example, with respect to temperature, the term "about" can mean the stated temperature plus or minus 0.05° C.

An azeotropic or azeotrope-like composition of the present invention can be used in polymerization mediums suitable to polymerize one or more monomers to form a polymer, or alternatively, a polymerization medium in accordance with the present invention which is not azeotropic or azeotrope-like can be transformed into an azeotropic or azeotrope-like composition of the present invention through the simple addition of either trans-HFO-1234ze or isobutylene. For example, a polymerization medium in accordance with the present invention can comprise at least one catalyst, isobutylene and trans-HFO-1234ze. Preferably, the at least one catalyst comprises a Lewis acid, including but not limited to Lewis acids comprising aluminum, boron, gallium, or indium. For example, alkyl aluminum halides, boron halides, and organo-boron halides can be suitable catalysts. Some additional non-limiting examples of suitable Lewis acids are provided in U.S. Patent Application Publication No. 2005/0101751, the disclosure of which is hereby incorporated by reference.

Azeotropic or azeotrope-like compositions of isobutylene and trans-HFO-1234ze can be used in polymerization processes to produce polymers of one or more monomers. Such a polymerization process can include, for example, providing isobutylene by itself or in combination with other monomers, and contacting the isobutylene or the monomer mixture in a reactor with at least one catalyst in the presence of trans-HFO-1234ze in an amount which forms an azeotropic or azeotrope-like composition of the present invention.

The compositions in accordance with the present invention improve the performance of the polymerization process, as well as the quality of a polymer product made therewith. As an initial matter, the compositions may be beneficially used to remove monomer from the reaction mixture. For example, at the end of a polymerization process, if an azeotropic or azeotrope-like composition is present, or is subsequently formed, the evaporation of solvent (e.g., trans-HFO-1234ze) facilitates the evaporation of monomer (e.g., isobutylene) from the mixture.

In addition, the compositions in accordance with the present invention may be used to address the problem with product agglomeration present in existing polymerization processes which use methyl chloride as a solvent. See, U.S. Pat. No. 7,423,100, column 42, paragraph 25. The compositions in accordance with the present invention could be used to improve product agglomeration properties during polymerization, i.e., by reducing, or possibly completely eliminating, the agglomeration of product.

EXAMPLE 1

An ebulliometer composed of a vacuum jacketed tube with a condenser on top of which was further equipped with a quartz thermometer. 16.36 grams of trans-HFO-1234ze was charged into the ebulliometer and the boiling point was observed. Isobutylene was then added in small increments, and the boiling point of each of the compositions was observed as the weight percentage of isobutylene was increased. A temperature depression was observed at about −20.23° C., indicating a binary minimum boiling azeotrope. The results are shown in Table 1.

TABLE 1

| Wt % trans-HFO-1234ze | Wt % isobutylene | T(° C.) |
|---|---|---|
| 100.00 | 0.00 | −19.46 |
| 99.76 | 0.24 | −19.49 |
| 98.85 | 1.15 | −19.63 |
| 95.62 | 4.38 | −20.01 |
| 90.99 | 9.01 | −20.19 |
| 87.82 | 12.18 | −20.23 |
| 84.72 | 15.28 | −20.17 |
| 82.05 | 17.95 | −20.11 |

TABLE 1-continued

| Wt % trans-HFO-1234ze | Wt % isobutylene | T(° C.) |
|---|---|---|
| 78.05 | 21.95 | −20.00 |
| 74.57 | 25.43 | −19.88 |
| 70.12 | 29.88 | −19.71 |
| 65.84 | 34.16 | −19.53 |
| 61.53 | 38.47 | −19.35 |
| 58.85 | 41.15 | −19.25 |
| 56.67 | 43.33 | −19.16 |
| 54.26 | 45.74 | −19.03 |
| 52.07 | 47.93 | −18.97 |
| 49.25 | 50.75 | −18.80 |

EXAMPLE 2

An ebulliometer composed of a vacuum jacketed tube with a condenser on top of which was further equipped with a quartz thermometer. 8.06 grams of isobutylene was charged into the ebulliometer and the boiling point was observed. trans-HFO-1234ze was then added in small increments, and the boiling point of each of the compositions was observed as the weight percentage of trans-HFO-1234ze was increased. No temperature depression was observed over the range of compositions tested. The results are shown in Table 2.

TABLE 2

| Wt % isobutylene | Wt % trans-HFO-1234ze | T(° C.) |
|---|---|---|
| 100.00 | 0.00 | −7.40 |
| 97.34 | 2.66 | −8.71 |
| 86.48 | 13.52 | −13.61 |
| 75.61 | 24.39 | −16.84 |
| 66.12 | 33.88 | −17.84 |
| 53.41 | 46.59 | −18.63 |
| 47.89 | 52.11 | −18.91 |
| 44.12 | 55.88 | −19.12 |

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A binary azeotropic or azeotrope-like composition consisting essentially of the two compounds isobutylene and trans-1,3,3,3-tetrafluoro-prop-1-ene.

2. The azeotropic or azeotrope-like composition of claim 1, wherein the composition comprises trans-1,3,3,3-tetrafluoroprop-1-ene in an amount from about 82% by weight of the composition to about 96% by weight of the composition.

3. The azeotropic or azeotrope-like composition of claim 2, wherein the composition comprises trans-1,3,3,3-tetrafluoroprop-1-ene in an amount from about 85% by weight of the composition to about 91% by weight of the composition.

4. The azeotropic or azeotrope-like composition of claim 3, wherein the wherein the composition comprises trans-1,3,3,3-tetrafluoroprop-1-ene in an amount from about 87% by weight of the composition to about 89% by weight of the composition.

5. The azeotropic or azeotrope-like composition of claim 1, wherein the azeotropic or azeotrope-like composition consists of isobutylene and trans-1,3,3,3-tetrafluoroprop-1-ene.

6. The azeotropic or azeotrope-like composition of claim 1, wherein the azeotropic or azeotrope-like composition has a boiling point of between about −20.23° C. and −20.00° C.

7. The azeotropic or azeotrope-like composition of claim 1, wherein the azeotropic or azeotrope-like composition has a boiling point of about −20.23° C.

8. A polymerization medium suitable to polymerize one or more monomers to form a polymer, the polymerization medium comprising:
at least one catalyst;
trans-1,3,3,3-tetrafluoroprop-1-ene; and
at least one monomer, said at least one monomer comprising isobutylene,
wherein said polymerization medium is an azeotropic or azeotrope-like composition, or may be transformed into an azeotropic or azeotrope-like composition through the addition of either trans-1,3,3,3-tetrafluoroprop-1-ene or isobutylene.

9. The polymerization medium of claim 8, wherein said at least one catalyst comprises a Lewis acid.

10. The polymerization medium of claim 8, wherein the azeotropic or azeotrope-like composition comprises trans-1,3,3,3-tetrafluoroprop-1-ene in an amount from about 82% by weight of the composition to about 96% by weight of the composition.

11. The polymerization medium of claim 8, wherein the azeotropic or azeotrope-like composition comprises trans-1,3,3,3-tetrafluoroprop-1-ene in an amount from about 85% by weight of the composition to about 91% by weight of the composition.

12. The polymerization medium of claim 8, wherein the azeotropic or azeotrope-like composition comprises trans-1,3,3,3-tetrafluoroprop-1-ene in an amount from about 87% by weight of the composition to about 89% by weight of the composition.

13. A polymerization process comprising the steps of:
providing one or more monomers, wherein at least one of said one or more monomers is isobutylene;
contacting the one or more monomers in a reactor with at least one catalyst in the presence of trans-1,3,3,3-tetrafluoroprop-1-ene, said trans-1,3,3,3-tetrafluoroprop-1-ene being present in an amount such that an azeotropic or azeotrope-like composition comprising said trans-1,3,3,3-tetrafluoroprop-1-ene and said isobutylene is present.

14. The polymerization process of claim 13, wherein said at least one catalyst comprises a Lewis acid.

15. The polymerization process of claim 13, wherein the azeotropic or azeotrope-like composition comprises trans-1,3,3,3-tetrafluoroprop-1-ene in an amount from about 82% by weight of the composition to about 96% by weight of the composition.

16. The polymerization process of claim 13, wherein the azeotropic or azeotrope-like composition comprises trans-1,3,3,3-tetrafluoroprop-1-ene in an amount from about 85% by weight of the composition to about 91% by weight of the composition.

17. The polymerization process of claim 13, wherein the azeotropic or azeotrope-like composition comprises trans-1,3,3,3-tetrafluoroprop-1-ene in an amount from about 87% by weight of the composition to about 89% by weight of the composition.

* * * * *